United States Patent [19]

ElSohly

[11] Patent Number: 4,933,363

[45] Date of Patent: Jun. 12, 1990

[54] METHOD FOR EFFECTING SYSTEMIC DELIVERY OF DELTA-9-TETRAHYDROCANNABINOL

[76] Inventor: Mahmoud A. ElSohly, 41 Sheila Dr., Oxford, Miss. 38655

[21] Appl. No.: 233,268

[22] Filed: Aug. 16, 1988

[51] Int. Cl.⁵ .............................................. A61K 31/35
[52] U.S. Cl. ...................................... 514/454; 549/390
[58] Field of Search .......................... 549/390; 514/454

[56] References Cited

U.S. PATENT DOCUMENTS

| | | | |
|---|---|---|---|
| 3,728,360 | 4/1973 | Pars et al. | 549/390 |
| 3,941,782 | 3/1976 | Harris et al. | 549/390 |
| 4,327,028 | 4/1982 | Kaplan | 549/390 |

OTHER PUBLICATIONS

Martin et al., NIDA Res. Monogr., 79, 108–22 (1987)—C.A., 108, 87591p (1988).
ElSohly et al., Curr. Eye Res., 3(6), 841–50 (1984)—C.A., 101, 65555h (1984).
Tsui et al., Can. J. Biochem., 52(3), 252–8 (1974)—C.A., 81, 102861w (1974).

*Primary Examiner*—Nicky Chan
*Attorney, Agent, or Firm*—William D. Stokes

[57] ABSTRACT

Compositions and method for accessing delta-9-tetrahydrocannabinol into the system of the body.

5 Claims, No Drawings

METHOD FOR EFFECTING SYSTEMIC DELIVERY OF DELTA-9-TETRAHYDROCANNABINOL

BRIEF DESCRIPTION OF INVENTION

The invention is directed to new compositions as a means for accessing therapeutic dosages of delta-9-tetrahydrocannabinol into the systemic system, and suppository compositions for effecting the systemic absorption of delta 9 tetrahydrocannabinol by a non-invasive method. The new compounds are polar esters of delta 9 tetrahydrocannabinol.

BACKGROUND OF THE INVENTION

Delta-9-tetrahydrocannabinol is the major psychologically active cannabinoid in the drug type cannabis. Since its discovery, numerous studies have been carried out to characterize the biologic activities of the compound. It has been demonstrated that the delta-9-tetrahydrocannabinol has important therapeutic applications as an anti emetic for patients undergoing chemotherapy regimens for cancer treatment and for lowering intraocular pressure in the treatment of glaucoma. For the most part, the studies have involved the intraperitoneal, intravenous, and intramuscular administration of the delta 9-tetrahydrocannabinol compound. These routes of administration have great disadvantages because of the lipophilic nature of the drug. For intraperitoneal and intramuscular administration, co-administration of an emulsifying agent is required. While an emulsifying agent may be used to administer the compound intravenously, the compound may be intravenously administered in small dosage units dissolved in human serum albumin. Oral administration of the drug has been extensively investigated by using, for example, chocolate cookies and sesame oil capsules as carriers. The bioavailability of the drug administered via the oral routes has been found to be quite low, and oral absorption of tetrahydrocannabinol has been found to also be slow and erratic. Moreover, absorption of delta-9 tetrahydrocannabinol from the gastrointestinal tract is decreased by fasting or food deprivation in addition to numerous other pathological conditions brought about by the condition being treated.

Studies have shown that there was no absorption, consequently no bioavailability achieved via the rectal route using various suppository formulations. In view of the low bioavailability, slow and erratic absorption coupled with extreme interpatient variability in absorption, oral administration as an effective route for administering tetrahydrocannabinol has generally been unreliable. Since no absorption has been obtained via the rectal route, administration dosage by suppository simply has not been a viable alternative. Prior to the present invention, the intramuscular route of administration of tetrahydrocannabinol would be the only alternative method; however, it will be appreciated that such method suffers from numerous disadvantages not the least of which the requirement for professional assistance which precludes self-medication.

SUMMARY OF THE INVENTION

In accordance with the invention, it has been discovered that a non-toxic polar ester of delta-9-tetrahydrocannabinol is readily absorbed from a suppository through the wall of the rectum. The inventive compounds are immediately hydrolyzed in the blood stream releasing the delta-9-tetrahydrocannabinol to provide the highest degree of bioavailability of the drug without regard to patient conditions and anomalies.

The invention further comprises compositions and a method for obtaining absorption of the compounds of the invention through the walls of the rectum consisting of administering a polar ester of delta-9-tetrahydrocannabinol in a pharmaceutically acceptable suppository composition. Examples of useful suppository bases include mixtures of mono, di, and triglycerides of naturally occurring fatty acids having a melting temperature that insures melting of the suppository within the rectum within reasonable time limits after insertion; polyoxyethylene ether emulsions; and mixtures of polyethylene glycols. The compounds of the invention are administered in non-toxic dosage concentrations sufficient to insure the release of a sufficient dosage unit of delta-9-tetrahydrocannabinol into the blood to provide the desired anti emetic results, or to result in the lowering of intraocular pressure of the patient when treating for glaucoma. The actual dosage administered will be determined by physical and physiological factors such as body weight, severity of condition, and idiopathy of the patient. With these considerations in mind, the dosage of releasable delta-9-tetrahydrocannabinol for a particular subject can be readily determined by the physician.

DETAILED DESCRIPTION OF THE INVENTION

The compounds used in the composition of the invention are represented by the formula

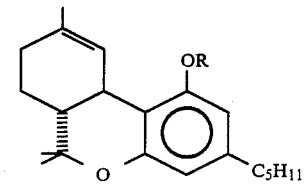

wherein R is an acyl group having a polar side chain, preferably R represents

and R' is an alkyl containing a carboxyl or amino group. In a preferred embodiment of the invention R is the hemisuccinic acid ester. Other useful polar esters are the hemi-ester of malonic acid and the alaninate ester of alanine. It has been found that salts of the terminal carboxylic acid group of the ester, for example, the N-methyl glucamine salt as well as the sodium and potassium salts are also useful.

EXAMPLE I

Delta-9-tetrahydrocannabinol hemisuccinate ester was prepared by refluxing delta-9-tetrahydrocannabinol in pyridine with excess succinic anhydride overnight. The reaction mixture was then brought to room temperature followed by evaporation of the pyridine under vacuum. The residue was chromatographed over silica gel column using hexane:ether (80:20) and the fraction containing the hemisuccinate ester collected. Evaporation of the solvent resulted in a thick, oily residue of the hemisuccinate ester.

The infrared spectrum exhibited strong OH absorbance between 3500–3100 cm$^{-1}$, a broad carbonyl absorption between 1770–1700 and aromatic absorption at 1625–1570 cm$^{-1}$. The proton NMR spectrum showed peaks at δ300MHZ (CDCl$_3$). 6.55 (d,J=1.5 Hz, 6.411 (d,J=1.5 Hz), 5.932 (s), 2.94–2.75 (m), 2.486 (t,J=8 Hz), 1.658 (s), 1.400 (s), 1.293 (m), 1.074 (s), and 0.876 (t,J=7 Hz). The $^{13}$C NMR showed peaks at δ75 MHz (CDCl$_3$): 177.885 (s), 170.013 (s), 154.500 (s), 149.199 (s), 142.763 (s), 134.819 (s), 123.278 (d), 115.348 (d), 115.057 (s), 113.858 (d), and other peaks at 45.614, 35.390, 34.077, 31.485, 31.019, 30.525, 29.173, 29.123, 28.870, 27.413, 24.892, 23.375, 22.507, 19.306, and 13.992.

The MS spectra showed a molecular ion at m/z 414 (4%) and a base peak at 231 with other significant ions at m/z 314 (43%), 299 (42%), 297 (90%), 295 (38%), 271 (37%), 258 (26%), and 243 (37%).

Methylation of delta 9 tetrahydrocannabinol hemisuccinate using diazomethane provided the methyl ester which was shown to be a single peak by GC/MS analysis using a capillary column (15M×0.25 mm DB-1 column) which showed a molecular ion at m/z 428 (6%), a base peak at m/z 297, and other significant ions at m/z 313 (50%), 314 (32%), 299 (26%), 243 (31%), 231 (22%), and 115 (52%).

Suppositories were prepared containing 15 mg delta-9-tetrahydrocannabinol hemisuccinate, an equivalent of 11.65 mg delta-9-tetrahydrocannabinol. The delta 9-tetrahydrocannabinol hemisuccinate was formulated in several different suppository bases, including the following:

1. Witepsol-H15; a mixture of mono, di, and triglycerides of naturally occurring fatty acids (C$_{10}$–C$_{18}$) with a melting range of 32°–35°.
2. Cetomacrogol-1000, a polyoxyethylene cetyl ether which is an emulsion forming base with surface activity that might act by affecting the permeability of the cell membranes.
3. A mixture of Polyethylene glycols—PEG 3350 (25%) and PEG-600 (75%), a commonly used water soluble base which releases active ingredients by dissolving in fluids in the rectal area.

The suppositories were administered to monkeys and blood samples were collected for twenty four hour periods following administration. Blood samples were collected at 0, 5, 15, 30, 60, 120, 180, 240, 300, 360, and 480 minutes, then at 24 hours. Plasma samples were analyzed from each of the blood collections for delta-9-tetrahydrocannabinol and its major metabolite, 11- nor delta-9-tetrahydrocannabinol-9-carboxylic acid (THC-COOH). The bioavailability of delta-9-tetrahydrocannabinol from these suppositories was compared with oral administration of delta-9-tetrahydrocannabinol in sesame seed oil. In addition, intravenous administration of delta-9-tetrahydrocannabinol in ethanol solution was compared with equal intravenous dosage units of the delta-9-tetrahydrocannabinol-hemisuccinate ester. The comparisons were carried out in a randomized 4×4 Latin square design in monkeys.

EXAMPLE II

Delta-9-tetrahydrocannabinol hemisuccinate was formulated in three different suppository bases, as discussed above. One suppository from each formulation was administered to each of three different monkeys. Blood samples were collected for a 24-hour period at 0 (immediately after dosing), 15, 30, 60, 120, 240, and 360 minutes and then at 24 hours. Samples were then analyzed for delta 9-tetrahydrocannabinol using radioimmunoassay (RIA) kits provided by the National Institute on Drug Abuse (NIDA) which are specific for the drug. Table I shows the blood levels of delta-9-tetrahydrocannabinol at each time interval after administration of one suppository for each formulation.

TABLE I

Concentration of delta-9-tetrahydrocannabinol in plasma samples collected at different time intervals from monkeys administered delta-9-tetrahydrocannabinol hemisuccinate in different suppository bases.
Delta-9-tetrahydrocannabinol (ng/mL)[1]

| Time | Witepsol-H15 | Cetomacrogol-1000 | PEG-3350/PEG-600 25:75 |
|---|---|---|---|
| 0 | 2.2 | 2.2 | 0.9 |
| 0.25 hr | 17.6 | 2.5 | 20.7 |
| 0.5 hr | 37.3 | 1.8 | 34.3 |
| 1 hr | 49.2 | 3.6 | 35.9 |
| 2 hr | 42.4 | 2.2 | 27.9 |
| 4 hr | 43.3 | 4.8 | 13.3 |
| 6 hr | 27.4 | 5.5 | 9.8 |
| 24 hr | 2.5 | 1.7 | 2.9 |

EXAMPLES II–V

Delta-9-tetrahydrocannabinol hemisuccinate was prepared in a suppository formulation using Witepsol-H15 as the base and at a concentration of 13.5 mg of the ester/suppository (equivalent to 10 mg of the parent drug/suppository). Four suppositories were administered each to a different monkey at different times (two weeks apart). Blood samples were collected at 0 (immediately following administration), 5, 15, 30, 60, 90, 120, 180, 240, 360, and 480 minutes and then at 24 hours. These samples were analyzed by GC/MS for the parent drug (delta-9-tetrahydrocannabinol) as well as for its metabolite 11-nor-delta-9-tetrahydrocannabinol-9-COOH.

Tables II and III show the blood levels of delta -9-tetrahydrocannabinol and its metabolite, respectively, from the four animals tested.

TABLE II

Apparent delta-9-tetrahydrocannabinol levels (ng/mL) in plasma as determined by GC/MS following rectal administration of delta-9-tetrahydrocannabinol hemisuccinate via a suppository.

| Time (hr) | Animal Number | | | | Mean |
|---|---|---|---|---|---|
| | 1 | 2 | 3 | 4 | |
| 0.0 | 0 | 0 | 0 | 0 | 0.0 |
| 0.1 | 0 | 0 | 0 | 0 | 0.0 |
| 0.25 | 11 | 23 | 10 | 15 | 14.8 |
| 0.5 | 31 | 41 | 35 | 27 | 33.5 |
| 1.0 | 46 | 61 | 61 | 16 | 46.0 |
| 1.5 | 45 | 69 | 86 | 14 | 53.5 |
| 2.0 | 44 | 77 | 77 | 15 | 53.3 |
| 3.0 | 43 | 88 | 58 | 11 | 50.0 |
| 4.0 | 65 | 50 | 32 | 5 | 38.0 |
| 6.0 | 43 | 18 | 13 | 0 | 18.5 |
| 8.0 | 9 | 12 | 30 | 0 | 12.8 |
| 24.0 | 3 | 0 | 2 | 0 | 1.3 |

TABLE III

Apparent 11-nor-delta-9-tetrahydrocannabinol-9-COOH levels (ng/mL) in plasma as determined by GC/MS following rectal administration of delta-9-tetrahydrocannabinol hemisuccinate via a suppository.

| Time (hr) | Animal Number | | | | Mean |
|---|---|---|---|---|---|
| | 1 | 2 | 3 | 4 | |
| 0.0 | 0 | 0 | 0 | 0 | 0.0 |
| 0.1 | 0 | 0 | 0 | 0 | 0.0 |
| 0.25 | 0 | 0 | 0 | 0 | 0.0 |

TABLE III-continued

Apparent 11-nor-delta-9-tetrahydrocannabinol-9-COOH levels (ng/mL) in plasma as determined by GC/MS following rectal administration of delta-9-tetrahydrocannabinol hemisuccinate via a suppository.

| Time (hr) | Animal Number | | | | Mean |
|---|---|---|---|---|---|
| | 1 | 2 | 3 | 4 | |
| 0.5 | 2 | 3 | 4 | 3 | 3.0 |
| 1.0 | 9 | 16 | 19 | 8 | 13.0 |
| 1.5 | 11 | 28 | 36 | 13 | 22.0 |
| 2.0 | 17 | 35 | 52 | 15 | 29.8 |
| 3.0 | 22 | 47 | 86 | 12 | 41.8 |
| 4.0 | 29 | 44 | 69 | 14 | 39.0 |
| 6.0 | 42 | 34 | 57 | 8 | 35.3 |
| 8.0 | 42 | 22 | 67 | 8 | 34.8 |
| 24.0 | 36 | 24 | 39 | 3 | 25.5 |

EXAMPLE VI

The parent drug delta-9-tetrahydrocannabinol was formulated in a suppository form at 10 mg/suppository using Witepsol-H15 as the base. One suppository was administered to a monkey and blood samples collected at the same time intervals as shown under Examples II-V. GC/MS analysis of these samples was carried out for delta-9-tetrahydrocannabinol and its metabolite. Neither delta-9-tetrahydrocannabinol nor its metabolite was detected in any of the blood samples, confirming the lack of bioavailability of delta-9-tetrahydrocannabinol itself from a suppository dosage form.

EXAMPLES VII-XVIII

The four monkeys used in Examples II-V were used in a randomized 4×4 Latin square design to compare the bioavailability of delta 9-tetrahydrocannabinol from a suppository formulation containing the hemisuccinate ester with a sesame seed oil formulation containing the parent drug, and further the intravenous (i.v.) administration of the hemisuccinate ester with an equivalent i.v. dose of the parent drug. Each monkey received a 10 mg oral dose of delta-9-tetrahydrocannabinol, a 0.5 mg/kg i.v. dose of delta-9-tetrahydrocannabinol, an i.v. dose of the hemisuccinate equivalent to 0.5 mg/kg of the parent drug or the suppositories of the hemisuccinate. Blood samples were collected from each animal following the same schedule outlined under Examples II-V. All blood samples were analyzed by GC/MS for delta-9-tetrahydrocannabinol and its acid metabolite.

Table IV shows the mean concentration of delta-9-tetrahydrocannabinol in the various blood samples at each time interval from each route of administration, while Table V shows the mean concentration of the acid metabolite in these samples. The examples clearly reveal the equivalency of the intravenous dosage of the hemisuccinate ester of delta-9-tetrahydrocannabinol to the intravenous dosage of the parent delta-9-tetrahydrocannabinol. Moreover, the examples clearly reveal the extraordinary superiority of the inventive suppository dosage unit form of the delta-9-tetrahydrocannabinol hemisuccinate in delivering the delta-9-tetrahydrocannabinol to the blood over orally administered sesame seed oil formulation of the delta-9-tetrahydrocannabinol per se.

TABLE IV

Mean delta-9-tetrahydrocannabinol levels (ng/mL) in plasma of four monkeys as determined by GC/MS following administration of the various formulations.

| Time (hr) | I.V. THC | I.V. THC Ester | Oral THC in Sesame Oil | THC Ester in Suppository |
|---|---|---|---|---|
| 0.0 | 0.0 | 0.0 | 0.0 | 0.0 |
| 0.1 | 1677.3 | 2060.3 | 0.0 | 0.0 |
| 0.25 | 334.8 | 669.3 | 0.0 | 14.8 |
| 0.5 | 169.8 | 251.3 | 0.0 | 33.5 |
| 1.0 | 101.8 | 95.8 | 0.0 | 46.0 |
| 1.5 | 67.3 | 65.3 | 0.0 | 53.5 |
| 2.0 | 55.8 | 42.5 | 0.0 | 53.3 |
| 3.0 | 34.0 | 26.3 | 0.5 | 50.0 |
| 4.0 | 22.8 | 18.5 | 1.3 | 38.0 |
| 6.0 | 29.0 | 13.0 | 2.3 | 18.5 |
| 8.0 | 17.3 | 8.0 | 4.3 | 12.8 |
| 24.0 | 2.5 | 2.5 | 0.8 | 1.3 |

EXAMPLE XIX

The N-methyl glucamine salt of delta 9-tetrahydrocannabinol hemisuccinate ester was prepared by combining equimolar amounts of N methyl glucamine with the hemisuccinate ester in ethanol followed by evaporation of the solvent. The resulting salt was then prepared in a suppository formulation using Witepsol-H15 as the base and at a concentration equivalent to 13.5 mg of the ester per suppository (equivalent to 10 mg of the parent drug per suppository). One suppository was then administered to a monkey and blood samples were collected at 0, 15, 30, 60, 120, 240, 360, and 480 minutes and then at 24 hours. These samples were analyzed by GC/MS for the parent drug (delta-9-tetrahydrocannabinol) as well as for its metabolite, 11-nor-delta-9-tetrahydrocannabinol-9-COOH. The results were compared with those obtained from the administration of a suppository containing an equivalent amount of the hemisuccinate ester in the free form (not as a salt) to another monkey. Table VI shows that the blood levels in both cases are virtually equivalent and therefore support the fact that either the free ester or a salt thereof could be used in suppository formulation.

TABLE V

Mean delta-9-tetrahydrocannabinol acid metabolite levels (ng/ml) in plasma of four monkeys as determined by GC/MS following administration of the various formulations.

| Time (hr) | I.V. THC | I.V. THC Ester | Oral THC in Sesame Oil | THC Ester in Suppository |
|---|---|---|---|---|
| 0.0 | 0.0 | 0.0 | 0.0 | 0.0 |
| 0.1 | 21.3 | 19.5 | 0.0 | 0.0 |
| 0.25 | 126.3 | 118.0 | 0.0 | 0.0 |
| 0.5 | 161.3 | 109.5 | 0.0 | 3.0 |
| 1.0 | 162.8 | 111.8 | 0.0 | 13.0 |
| 1.5 | 160.3 | 110.8 | 0.0 | 22.0 |
| 2.0 | 150.8 | 94.3 | 0.0 | 29.8 |
| 3.0 | 130.3 | 90.0 | 2.5 | 41.8 |
| 4.0 | 129.5 | 69.5 | 7.8 | 39.0 |
| 6.0 | 84.7 | 54.8 | 13.8 | 35.3 |
| 8.0 | 74.5 | 33.3 | 12.8 | 34.8 |
| 24.0 | 31.3 | 24.5 | 22.3 | 25.5 |

TABLE VI

Concentration of delta-9-tetrahydrocannabinol in blood from monkeys administered suppositories containing the hemisuccinate ester as its N-methyl glucamine salt.

| | Delta-9-THC-Hemisuccinate Suppository | | Delta-9-THC Hemisuccinate-N Methyl Glucamine Salt Suppository | |
|---|---|---|---|---|
| Time (Min) | THC (ng/mL) | THC-Acid Metabolite (ng/mL) | THC (ng/mL) | THC-Acid Metabolite (ng/mL) |
| 0 | 0 | 14 | 0 | 0 |
| 15 | 18 | 29 | 0 | 0 |
| 30 | 33 | 33 | 22 | 16 |
| 60 | 31 | 33 | 53 | 8 |
| 120 | 19 | 15 | 35 | 21 |
| 240 | 26 | 29 | 32 | 55 |
| 360 | 8 | 15 | 20 | 23 |
| 480 | 8 | 12 | 39 | 32 |
| 1440 | 4 | 8 | 14 | 24 |

The invention has been described with reference to specific and preferred embodiments. It will be recognized by those skilled in the art that numerous changes and substitutions may be made without departing from the spirit and scope of the invention.

What is claimed is:

1. A method of alleviating nausea in mammals comprising administering rectally a therapeutically effective amount of a composition consisting essentially of a compound of the formula

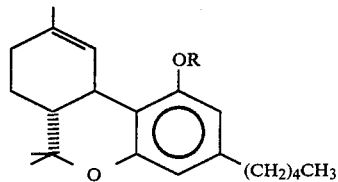

wherein R represents

and R' is an alkyl containing a carboxyl or amino group in a pharmaceutically acceptable rectal suppository formulation.

2. A method of reducing intraocular pressure in mammals comprising administering rectally a therapeutically effective amount of a composition consisting essentially of a compound of the formula

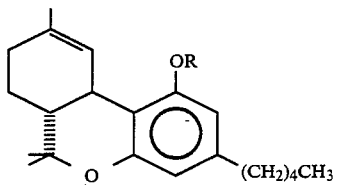

wherein R represents

and R' is an alkyl containing a carboxyl or amino group in a pharmaceutically acceptable rectal suppository formulation.

3. The method of claim 1 or 2 wherein R is the hemiester of succinic acid.

4. The method of claim 1 or 2 wherein R is the hemiester of malonic acid.

5. The method of claim 1 or 2 wherein R is the alaninate ester of alanine.

* * * * *

UNITED STATES PATENT AND TRADEMARK OFFICE
CERTIFICATE OF CORRECTION

PATENT NO. : 4,933,363
DATED : June 12, 1990
INVENTOR(S) : Mahmoud A. Elsohly It is certified that error appears in the above-identified patent and that said Letters Patent is hereby corrected as shown below:

ON THE TITLE PAGE:   After Item [54] insert;

-- This invention was made with government support under National Institute on Drug Abuse SBIR Grant #1 R43 DA04469. The government has certain rights in the invention. --

Signed and Sealed this

Twelfth Day of January, 1993

*Attest:*

DOUGLAS B. COMER

*Attesting Officer*   *Acting Commissioner of Patents and Trademarks*